United States Patent
Sobotta et al.

(10) Patent No.: US 7,321,042 B2
(45) Date of Patent: Jan. 22, 2008

(54) PROCESS FOR PREPARING N-SUBSTITUTED 3-β-AMINONORTROPANES

(75) Inventors: Rainer Sobotta, Ingelheim (DE); Hans-Peter Ignatow, Ingelheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 495 days.

(21) Appl. No.: 10/958,047

(22) Filed: Oct. 4, 2004

(65) Prior Publication Data
US 2005/0096346 A1    May 5, 2005

(30) Foreign Application Priority Data
Oct. 16, 2003 (DE) .................... 103 48 112
Mar. 18, 2004 (DE) .................... 10 2004 013 227

(51) Int. Cl.
*C07D 451/02* (2006.01)

(52) U.S. Cl. .................................................. 546/124

(58) Field of Classification Search ............... 546/124
See application file for complete search history.

(56) References Cited

FOREIGN PATENT DOCUMENTS

WO    WO 01/66521 A1    9/2001

OTHER PUBLICATIONS

Kajita et al., Pharmacology, Pharmacological characterization of a novel 5-HT4 receptor agonist, TS-951, 2001, vol. 63, pp. 8-16.*
Archer et al., 3a-(2-Diethylaminoethyl)-aminotropane and Related Compounds, Journal of the American Chemical Society, 1957, vol. 79, pp. 4194-4198.*
Burks, J. E., "Development of a Manufacturing Process for Zatosetron Maleate"; Organic Process Research & Development, 1997, vol. 1, pp. 198-210.
Nuhrich, A., et al; "Synthesis and binding affinities of a series of 1,2-benzisoxazole-3-carboxamides to dopamine and serotonin receptors"; Eur. J. Med. Chem., (1996) 31, pp. 957-964.
Archer, S. et al; "The Action of Nucleophilic Agents on 3 alpha-Chlorotropane"; J. Am. Chem. Soc., vol. 80, pp. 4677-4681.
Lewin, A. H. et al; "Molecular Features Associates with Polyamine Modulation of NMDA Receptors"; J. Med. Chem. 1998, 41, pp. 988-995.

* cited by examiner

*Primary Examiner*—Margaret D. Seaman
*Assistant Examiner*—Niloofar Rahmani
(74) *Attorney, Agent, or Firm*—Michael P. Morris; Mary-Ellen M. Devlin; Philip I. Datlow

(57) ABSTRACT

The invention relates to a process for preparing N-substituted 3β-aminonortropanes of formula I

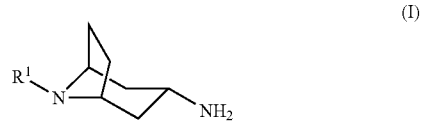

wherein $R^1$ has the meaning given in the claims, from the corresponding 3-oxonortropane or the corresponding 3α-aminonortropane, in which the latter is converted with an arylmethylamine or an arylaldehyde into the corresponding imines which are then tautomerised or isomerised and then hydrolysed.

The invention also relates to the new compounds of formula V

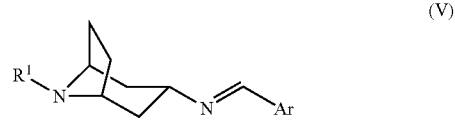

wherein $R^1$ and Ar have the meanings given in the claims.

7 Claims, No Drawings

PROCESS FOR PREPARING N-SUBSTITUTED 3-β-AMINONORTROPANES

TECHNICAL FIELD

The invention relates to a process for preparing N-substituted 3β-aminonortropanes of formula I

(I)

wherein $R^1$ has the meaning given in the claims, from the corresponding 3-oxonortropane or the corresponding 3α-aminonortropane, in which the latter is converted with an arylmethylamine or an arylaldehyde into the corresponding imines which are then tautomerised or isomerised and then hydrolysed.

BACKGROUND OF THE INVENTION

The compounds of formula I are valuable intermediate products in the chemical synthesis of various pharmaceutical active substances (e.g. A. Nuhrich et al., Eur. J. Med. Chem. 31, 12, 1996, 957-964), or are pharmaceutical active substances themselves, particularly NMDA receptor modulators (e.g. A. H. Lewin et al., J. Med. Chem, 1998, 41, 988-995).

By hydrogenation of tropanone-oximes in the presence of a platinum catalyst and a diluent under elevated pressure (e.g. S. Archer, J. Am. Chem. Soc. 80, 1958, 4677), N-substituted 3-aminonortropanes are predominantly obtained in the α form.

By reacting tropanone-oximes with metallic sodium in an alcohol (e.g. A. Nuhrich et al., loc. cit) predominantly the β-isomers of the N-substituted 3-aminonortropanes are obtained.

However, this process is of only limited use for large-scale industrial production for safety reasons.

The aim of the present invention was therefore to propose a method of producing N-substituted 3β-aminonortropanes of formula I which can be carried out on an industrial scale, with high yields and with favourable space/time ratios. The invention also set out to provide 3β-aminonortropanes of formula I which are substantially free from the corresponding 3α-isomers.

This objective was achieved according to the invention by the provision of a process in which the 3β-aminonortropane is obtained starting from a correspondingly substituted 3-oxonortropane or a correspondingly substituted 3α-aminonortropane.

The process according to the invention makes it possible to prepare 3β-aminonortropanes on an industrial scale in a high yield and purity.

BRIEF SUMMARY OF THE INVENTION

The invention relates to a process for preparing N-substituted 3β-aminonortropanes of formula I or an acid addition salt thereof,

(I)

wherein
$R^1$ denotes an optionally substituted group selected from the group consisting of $C_1$-$C_8$-alkyl, $C_2$-$C_8$-alkenyl, $C_3$-$C_8$-cycloalkyl and $C_6$-$C_{10}$-aryl-$C_1$-$C_8$-alkyl,
wherein either
(a) a corresponding 3-oxonortropane of formula IIA

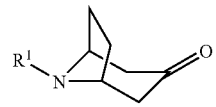
(IIA)

is reacted with an arylmethylamine of formula IIIA

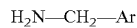
(IIIA)

wherein
Ar denotes an optionally substituted phenyl group or an optionally substituted 5- or 6-membered heteroaromatic group with at least one heteroatom selected from the group N, O and S; or
(b) a corresponding 3α-aminonortropane of formula IIB

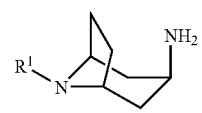
(IIB)

is reacted with an arylaldehyde of formula IIIB

(IIIB);

the imine of formulae IVA or IVB

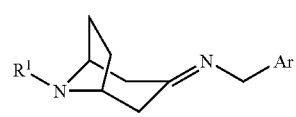
(IVA)

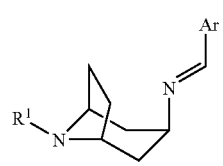
(IVB)

obtained in each case is converted into the thermodynamically stable tautomer or isomer of formula V

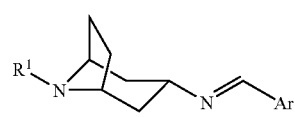
(V)

then hydrolysed and optionally converted into an acid addition salt.

The invention further relates to the new compounds of formula V

(V)

wherein $R^1$ and Ar have the meanings specified, as well as the tautomers or isomers of formulae IVA and IVB.

DETAILED DESCRIPTION OF THE INVENTION

The term $C_1$-$C_8$-alkyl on its own or in connection with other groups or radicals represents hereinbefore and hereinafter a straight-chain or branched alkyl group with 1 to 8 C atoms, preferably 1 to 6 C atoms, particularly 1 to 4 C atoms. Examples include methyl, ethyl, n-propyl, isopropyl, n-butyl, sec-butyl, isobutyl, tert-butyl, n-pentyl, neopentyl and n-hexyl. Methyl and ethyl are most particularly preferred.

The term $C_2$-$C_8$-alkenyl hereinbefore and hereinafter denotes a straight-chain or branched alkenyl group with 2 to 8 C atoms, preferably 2 to 6 C atoms, particularly 2 to 4 C atoms. Examples include vinyl, prop-1-enyl, prop-2-enyl (allyl), but-1-enyl and pent-1-enyl. Vinyl and allyl are most particularly preferred.

The term $C_3$-$C_8$-cycloalkyl hereinbefore and hereinafter denotes a cycloalkyl group with 3 to 8 C atoms, preferably 3 to 6 C atoms, particularly 5 or 6 C atoms. Examples include cyclopropyl, cyclobutyl, cyclopentyl and cyclohexyl.

The term $C_6$-$C_{10}$-aryl on its own or in connection with other groups or radicals hereinbefore and hereinafter denotes a phenyl or naphthyl group optionally substituted by $C_1$-$C_6$-alkyl, $C_1$-$C_6$-alkoxy, amino, $C_1$-$C_6$-alkylamino, di-($C_1$-$C_6$-alkyl)-amino or halogen, preferably unsubstituted phenyl or phenyl substituted by 1 to 3 substituents selected from the group consisting of $C_1$-$C_4$-alkyl, $C_1$-$C_4$-alkoxy, amino, $C_1$-$C_4$-alkylamino and di-($C_1$-$C_4$-alkyl)-amino The group Ar denotes an aryl group as hereinbefore defined or a 5- or 6-membered heteroaromatic group which may be unsubstituted or substituted by $C_1$-$C_6$-alkyl, $C_1$-$C_6$-alkoxy, amino, $C_1$-$C_6$-alkylamino, di-($C_1$-$C_6$-alkyl)-amino or halogen with at least one heteroatom selected from the group N, O, and S.

Preferably the heteroaromatic group denotes pyrrole, furan, thiophene, imidazole, pyrazole, thiazole, thiadiazole, tetrazole, pyridine, pyrimidine or pyrazine.

The preferred process according to the invention is the process wherein $R^1$ denotes a group selected from the group consisting of $C_1$-$C_6$-alkyl, particularly methyl or ethyl and phenyl-$C_1$-$C_3$-alkyl, particularly benzyl.

Also preferred is the process according to the invention wherein Ar denotes a phenyl group which is mono- or disubstituted by $C_1$-$C_6$-alkoxy, particularly methoxy, ethoxy or isopropoxy and/or di-($C_1$-$C_6$-alkyl)-amino, particularly dimethylamino or diethylamino. Most particularly preferably, these substituents are located in the para position in relation to the methylamino group (formula IIIA) or the carbaldehyde group (formula IIIB).

Preferably the individual steps of the process according to the invention are carried out in each case in an inert diluent selected from the group consisting of optionally halogenated hydrocarbons such as for example benzene, toluene, xylene, methylcyclohexane or dichloromethane, amides such as for example acetamide or dimethylacetamide, nitriles such as for example acetonitrile or propionitrile, sulphoxides such as for example dimethylsulphoxide (DMSO), ethers such as for example diethyl ether, tert-butylmethylether (TBME) or tetrahydrofuran (THF) and mixtures thereof.

In a preferred embodiment of the process according to the invention the reaction between the compound of formula IIA and the compound of formula IIIA or between the compound of formula IIB and the compound of formula IIIB is carried out under dehydrating conditions.

As a rule 0.5 to 2.0 equivalents, preferably 0.8 to 1.2 equivalents of a compound of formula IIA or IIB are reacted, based on one equivalent of formula IIIA or IIIB. Preferably, roughly equimolar amounts of compounds of formula IIA or IIB are used, based on formula IIIA or IIIB.

Examples of dehydrating conditions include carrying out the reactions in the presence of water-binding agents such as for example phosphorus pentoxide, titanium tetrachloride or a molecular sieve or reacting in the presence of an inorganic or organic acid at elevated temperature and eliminating the water formed by azeotropic distillation. It is particularly preferable to eliminate the water using p-toluenesulphonic acid (p-TsOH) in toluene.

Preferably the imines of formulae IVA or IVB obtained in the reaction are converted into the tautomer of formula V in the presence of a base.

Particularly preferred are the new imines of formula VI

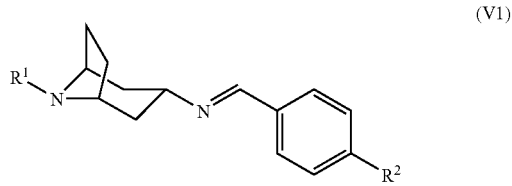

(VI)

wherein $R^1$ has the meaning given for formula I, and
$R^2$ denotes H, $C_1$-$C_6$-alkoxy, particularly methoxy or di-($C_1$-$C_6$-alkyl)-amino, particularly dimethylamino.

Suitable bases are strong bases, particularly metal alkoxides such as for example sodium methoxide, sodium ethoxide, potassium ethoxide, sodium tert-butoxide, potassium tert-butoxide, sodium neopentoxide, potassium neopentoxide, particularly potassium tert-butoxide.

As a rule the isomerisation is carried out in the presence of an inert diluent. Polar aprotic solvents are preferred such as for example dimethylsulphoxide, acetonitrile, dimethylacetamide, N,N-dimethylethylene urea (DEPU), N,N-dimethylpropylene urea (DMPU) or mixtures thereof. In a particularly preferred embodiment the reaction is carried out with potassium tert-butoxide in the presence of THF and DMSO.

The reaction is generally carried out at a temperature from 0 to 120° C., preferably at 25 to 100° C., particularly at 40 to 80° C. Under the conditions specified the isomerisation is complete in 1 to 15 hours.

As a rule the hydrolysis of the compound of formula IV is carried out in the presence of an acid. Strong inorganic or organic acids are preferred, such as for example sulphuric acid, hydrochloric acid, phosphoric acid or trifluoroacetic acid. It is particularly preferable to carry out the hydrolysis in a two-phase system consisting of an organic, slightly water-miscible solvent, particularly toluene or dichloromethane, water and the corresponding acid, particularly sulphuric acid.

The hydrolysis is generally carried out at a temperature from 0 to 100° C., preferably at 10 to 60° C., particularly at 15 to 30° C. Under the conditions specified the hydrolysis is complete in 15 to 360 minutes.

In a particularly preferred embodiment the aqueous phase of the crude product thus obtained is separated off, and made slightly alkaline with a suitable base, preferably an alkali metal hydroxide, particularly sodium hydroxide solution, preferably to a pH of 7.5 to 9.5, particularly about 8.0. The aqueous phase thus obtained is extracted with a water-immiscible solvent, preferably an aliphatic or aromatic hydrocarbon, particularly toluene. The organic phase thus obtained may be used to recover the starting materials.

The aqueous phase is separated off, and made strongly alkaline, preferably to a pH of 10.0 to 14.0, particularly about 12.7, with a suitable base, preferably an alkali metal hydroxide, particularly sodium hydroxide solution. The aqueous phase thus obtained is extracted with a water-immiscible solvent, preferably an optionally halogenated, aliphatic or aromatic hydrocarbon, particularly toluene or dichloromethane. The combined organic phases thus obtained are concentrated. In this way the compound of formula I is obtained in the form of the free base.

This may be converted into the corresponding acid addition salt by known methods, by treating with an inorganic or organic acid. Preferably for this purpose the free base is taken up in a polar solvent, preferably an alcohol such as for example methanol, ethanol or isopropanol, water or a mixture thereof, particularly a mixture of ethanol and water and adjusted to a slightly basic pH with the corresponding acid, preferably an inorganic acid such as hydrochloric acid or sulphuric acid.

The precipitate of the salt thus formed is separated off, washed with a polar solvent and dried. In this way the product is obtained in pure crystalline form without any further purification.

Other advantageous aspects of the procedure according to the invention are the high space/time yield in the present process and also the high yield and purity of the intermediate products, which can be further processed without chromatographic purification.

The Examples that follow serve to illustrate processes for preparing the compound of formula I carried out by way of example. They are to be understood only as possible procedures described by way of example without limiting the invention to their contents.

EXAMPLE 1

N-methyl-3-β-aminonortropane hemisulphate

A mixture of 17.0 g N-methyl-3-α-aminonortropane, 18.7 g 4-dimethylamino-benzaldehyde, 125 ml of toluene and 0.125 g p-TsOH is heated to boiling for 5 hours using the water separator. The reaction mixture is evaporated down. 36.2 g of N-methyl-3-α-(4-dimethylaminobenzylideneamino)-tropane is obtained, which is further processed without any further purification.

A mixture of 36.2 g N-methyl-3-α-(4-dimethylaminobenzylideneamino)-tropane, 100 ml DMSO, 13.8 g of a 24% solution of potassium tert-butoxide in THF is heated to 65 to 70° C. for 10 hours. The reaction mixture is stirred into 500 ml acetonitrile and filter washed with acetonitrile. The filter residue is dissolved in 300 ml of toluene and slowly stirred into a mixture of 200 ml of water and 10 ml concentrated sulphuric acid.

After 45 minutes' stirring at ambient temperature the phases are separated, the aqueous phase is adjusted to pH 8.0 with sodium hydroxide solution and washed with 100 ml of toluene. The phases are separated and the aqueous phase is combined with 150 ml dichloromethane and adjusted to pH 12.9 with sodium hydroxide solution, the phases are separated and the aqueous phase is extracted three times with 150 ml dichloromethane. The combined organic phases are concentrated. 8.8 g of a brown oil are obtained. This oil is taken up in 150 ml of ethanol, adjusted to pH 7.5-6.5 with semi-concentrated sulphuric acid and stirred for 1 hour at ambient temperature. 14.45 g of the salt are obtained with a decomposition point of 320° C.

EXAMPLE 2

N-methyl-3-β-aminonortropane hemisulphate

A mixture of 17.0 g N-methyl-3-α-aminonortropane, 17.0 g 4-methoxybenzaldehyde, 125 ml of toluene and 0.125 g p-TsOH is heated to boiling for 5 hours using a water separator. The reaction mixture is evaporated down. 33.5 g N-methyl-3-α-(4-methoxybenzylideneamino)-tropane is obtained, which is further processed without any further purification.

A mixture of 33.5 g N-methyl-3-α-(4-methoxybenzylideneamino)-tropane, 100 ml DMSO, 8.5 g of a 24% solution of potassium tert-butoxide in THF is heated to 65 to 70° C. for 5 hours. The reaction mixture is stirred into a mixture of 500 ml acetonitrile and 600 ml of water, extracted with three times 300 ml of toluene and concentrated. The residue is taken up in 200 ml of water, the aqueous phase is extracted with three times 200 ml dichloromethane. The combined extracts are concentrated, taken up in 200 ml of toluene and added dropwise to a solution of 10 ml concentrated sulphuric acid in 300 ml of water.

After 45 minutes' stirring at ambient temperature the phases are separated, the aqueous phase is adjusted to pH 8.0 with sodium hydroxide solution, extracted with 50 ml of toluene and twice with 50 ml dichloromethane. The aqueous phase is combined with 150 ml dichloromethane and adjusted to pH 12.9 with sodium hydroxide solution. The phases are separated and the aqueous phase is extracted with 6 times 60 ml dichloromethane. The combined organic phases are dried over sodium sulphate, filtered and concentrated. 17.1 g of a golden-brown oil are obtained. This oil is taken up in 200 ml of ethanol, adjusted to pH 7.0-6.5 with semi-concentrated sulphuric acid and stirred for 30 minutes at ambient temperature. 17.5 g of the salt are obtained with a decomposition point of 320° C.

EXAMPLE 3

N-benzyl-3-β-aminonortropane hemisulphate

A mixture of 75.5 g N-benzyl-nortropinone-hydrochloride, 60 ml of water, 173 ml of toluene and 22.5 ml sodium hydroxide solution is stirred at ambient temperature. The phases are separated and the aqueous phase is extracted with 87 ml of toluene. A mixture of the combined toluene phases, 41.2 g of 4-methoxybenzylamine and 0.22 g of p-TsOH is heated to boiling for 5 hours using a water separator. The reaction mixture is evaporated down. 95 g of N-benzyl-3-(4-methoxybenzylimino)-tropane is obtained, which is further processed without any further purification.

A mixture of 95 g of N-benzyl-3-(4-methoxybenzylimino)-tropane, 240 ml DMSO, 16.8 g of a 24% solution of potassium tert-butoxide in THF is heated to 65 to 70° C. for 5 hours. The reaction mixture is distributed between 300 ml of toluene and 900 ml of water, the aqueous phase is extracted twice with in each case 300 ml of toluene. The combined toluene phases are slowly stirred into a mixture of 960 ml of water and 21.7 ml of concentrated sulphuric acid.

After 60 minutes' stirring at ambient temperature the phases are separated, the aqueous phase is adjusted to pH 8.0 with sodium hydroxide solution, washed with 300 ml of toluene and saturated with common salt. The aqueous phase is combined with 150 ml dichloromethane and adjusted to pH 12.9 with sodium hydroxide solution, the phases are separated and the aqueous phase is extracted three times with 150 ml of toluene. The combined organic phases are concentrated. 54.5 g of the product are obtained in the form of a brown oil.

This is taken up in a mixture of 330 ml of ethanol and 6.67 ml of water and adjusted to pH 8.6 with 35 ml of a 32% sulphuric acid. The precipitate formed was filtered and washed with 265 ml of ethanol. The solid obtained is dried at 50° C. 53.8 g of the salt are obtained in the form of white crystals with a melting point of 283.4-284.9° C.

EXAMPLE 4

N-benzyl-3-β-aminonortropane hemisulphate

A mixture of 89.5 g of N-benzyl-3-α-aminonortropane dihydrochloride-hemihydrate, 100 ml of water and 172 ml of toluene is combined with 45 ml of a 45% sodium hydroxide solution and stirred. The phases are separated and the aqueous phase is extracted with 86 ml of toluene. The combined toluene phases are combined with 44.8 g of 4-dimethylaminobenzaldehyde and 0.22 g p-TsOH and heated to boiling for 4 hours using a water separator. The reaction mixture is evaporated down. 104.2 g of N-benzyl-3-α-(4-dimethylaminobenzylideneamino)-tropane is obtained which is further processed without any further purification.

A mixture of 104.2 g N-benzyl-3-α-(4-dimethylaminobenzylideneamino)-tropane, 239 ml of DMSO, 24 g of a 24% solution of potassium tert-butoxide in THF is heated to 65 to 70° C. for 4 hours and 15 minutes. The reaction mixture is distributed between 300 ml of toluene and 900 ml of water in which 21 g of common salt is dissolved, the aqueous phase is extracted twice with 300 ml of toluene in each case. The combined toluene phases are washed with 300 ml of water in which 7 g of common salt is dissolved. The organic phase thus obtained is slowly stirred into a mixture of 875 ml of water and 21.8 ml concentrated sulphuric acid.

After 60 minutes' stirring at ambient temperature the phases are separated, the aqueous phase is adjusted to pH 8.0 with sodium hydroxide solution and washed with 300 ml of toluene. The phases are separated and the aqueous phase is combined with 300 ml of toluene and adjusted to pH 12.7 with sodium hydroxide solution. The organic phase is separated off, and the aqueous phase is extracted twice with 300 ml of toluene. The combined organic phases from the extraction at pH 12.7 are concentrated. 58.77 g (90.6% of theory) of the product are obtained in the form of a yellowish oil.

This is taken up in a mixture of 330 ml of ethanol and 6.67 ml of water and adjusted to pH 8.6 with 35 ml of a 32% sulphuric acid. The precipitate formed is filtered and washed with 265 ml of ethanol. The solid obtained is dried at 50° C. 66.65 g (83.7% of theory) of the salt are obtained in the form of white crystals with a melting point of 283.4-284.9° C.

The invention claimed is:

1. A process for preparing N-substituted 3β-aminonortropanes of formula I or an acid addition salt thereof,

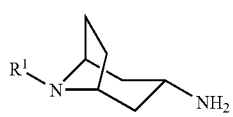
(I)

wherein
R$^1$ denotes an optionally substituted group selected from the group consisting of $C_1$-$C_8$-alkyl, $C_2$-$C_8$-alkenyl, $C_3$-$C_8$-cycloalkyl and $C_6$-$C_{10}$-aryl-$C_1$-$C_8$-alkyl,
wherein either
(a) a corresponding 3-oxonortropane of formula IIA

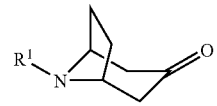
(IIA)

is reacted with an arylmethylamine of formula IIIA $$H_2N—CH_2—Ar \qquad (IIIA)$$

wherein
Ar denotes an optionally substituted phenyl group or an optionally substituted 5- or 6-membered heteroaromatic group with at least one heteroatom selected from the group N, O and S; or
(b) a corresponding 3α-aminonortropane of formula IIB

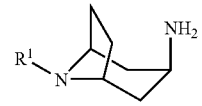
(IIB)

is reacted with an arylaldehyde of formula IIIB $$O═CH—Ar \qquad (IIIB);$$

converting the resulting imine of formulae IVA prepared in option (a) or IVB prepared in option (b)

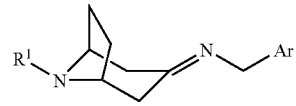
(IVA)

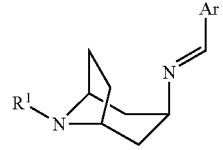
(IVB)

to the thermodynamically stable compound of formula V in the presence of a base

(V)

which is then hydrolysed in the presence of an acid to obtain the compound of formula I, which may be optionally converted into an acid addition salt.

2. The process according to claim 1, wherein R$^1$ denotes a group selected from the group consisting of $C_1$-$C_6$-alkyl and phenyl-$C_1$-$C_3$-alkyl.

3. The process according to claim 1, wherein Ar denotes a phenyl group mono- or disubstituted by $C_1$-$C_6$-alkoxy and/or di-($C_1$-$C_6$-alkyl)-amino.

4. The process according to claim 1, wherein the reaction between the compound of formula IIA and the compound of formula IIIA or between the compound of formula IIB and the compound of formula IIIB is carried out under dehydrating conditions.

5. The process according to claim 1, wherein the individual steps in each case are carried out in an inert diluent selected from the group consisting of optionally halogenated hydrocarbons, amides, nitriles, sulphoxides, ethers and mixtures thereof.

6. An N-substituted 3-β-(arylmethylidene)-aminonortropane of formula V

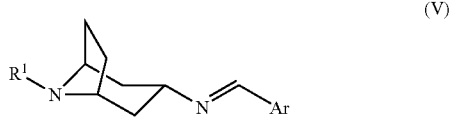

(V)

wherein
  $R^1$ denotes an optionally substituted group selected from the group consisting of $C_1$-$C_8$-alkyl, $C_2$-$C_8$-alkenyl, $C_3$-$C_8$-cycloalkyl and $C_6$-$C_{10}$-aryl-$C_1$-$C_8$-alkyl; and
  Ar denotes an optionally substituted phenyl group or an optionally substituted 5- or 6-membered heteroaromatic group with at least one heteroatom selected from the group N, O and S, or the tautomer or isomer thereof.

7. A 3-β(arylmethylidene)-aminonortropane of formula V according to claim 6, wherein $R^1$ denotes a group selected from the group consisting of $C_1$-$C_6$-alkyl and phenyl-$C_1$-$C_3$-alkyl, and Ar denotes unsubstituted phenyl or a phenyl group mono- or disubstituted by $C_1$-$C_6$-alkoxy and/or di-($C_1$-$C_6$-alkyl)-amino.

* * * * *